United States Patent [19] [11] 4,088,582
Murty et al. [45] May 9, 1978

[54] BLOOD PHASE SEPARATION MEANS

[75] Inventors: Vabilisetti S. Murty, Creve Coeur; Thomas C. Schuler, St. Louis, both of Mo.

[73] Assignee: Sherwood Medical Industries Inc., St. Louis, Mo.

[21] Appl. No.: 649,880

[22] Filed: Jan. 16, 1976

[51] Int. Cl.² ............................................. B01D 21/26
[52] U.S. Cl. .............................. 210/516; 23/258.5 R; 210/DIG. 23
[58] Field of Search ......... 210/83, 516, 518, DIG. 23, 210/DIG. 24; 23/230 B, 258.5 R, 259 R, 292; 128/214 R, 218 M, 272, DIG. 5; 233/1 A, 26

[56] References Cited
U.S. PATENT DOCUMENTS

| 3,780,935 | 12/1973 | Lukacs et al. | 210/83 X |
| 3,852,194 | 12/1974 | Zine, Jr. | 210/DIG. 23 |
| 3,909,419 | 9/1975 | Ayres | 210/DIG. 23 |
| 3,957,654 | 5/1976 | Ayres | 210/516 |
| 4,021,340 | 5/1977 | Zine, Jr. | 210/83 |

Primary Examiner—William A. Cuchlinski, Jr.
Attorney, Agent, or Firm—S. N. Garber; W. R. O'Meara

[57] ABSTRACT

A blood collection device includes a tube for receiving a sample of whole blood for centrifugal separation into the lighter phase, plasma or serum, and the heavier cellular phase. The tube has a needle-pierceable stopper at the opposite end for maintaining a negative pressure in the tube. A blood phase partitioning device is disposed within the tube and includes upper and lower members with the upper member having a greater specific gravity greater than that of the lower member but together having a specific gravity between that of the lighter phase and that of the heavier phase. A sealant is disposed between the members and in contact with each member and has a specific gravity equal to the average of the two members. During centrifugation of the blood, the partitioning device automatically moves to the interface of the two phases, and the members move toward each other forcing the sealant radially outwardly from between the members and against the inner wall of the tube to provide a permanent partition between the two separated phases.

6 Claims, 8 Drawing Figures

U.S.Patent    May 9, 1978    4,088,582

BLOOD PHASE SEPARATION MEANS

BACKGROUND OF THE INVENTION

This invention relates to fluid collection devices and more particularly to blood collection devices having means for partitioning the lighter and heavier phase of blood.

In the testing of blood samples, whole blood is usually drawn into an evacuated tube and the tube placed in a carriage for separating the lighter and heavier phases so that the lighter phase may be isolated and tested. Many different types of phase partitioning devices which provide a barrier or seal between the separated phases have been used or proposed for the purpose of allowing the lighter phase to be decanted or poured into a transfer tube free of cells, or to enable the two phases to remain in the collection tube without intermixing during shipment to a laboratory where the lighter phase is removed and subjected to analysis.

In U.S. Pat. No. 3,852,194 and U.S. Pat. No. 3,780,935, gel-like materials, such as a silicone material, is disposed in a collection tube, the gel-like material having a specific gravity between that of the lighter phase and that of the heavier phase so that it flows to the interface of the two phases and forms a partition between them. These devices generally require a relatively large amount of gel-like material, and in addition to the relatively high cost of the material, a relatively large surface area of the material is in contact with the blood components during and after centrifugation. This relatively large surface area of contact tends to increase the danger of interaction between the gel-like material and lighter blood phase which is to be analyzed. For example, collection tubes are used that employ silicone gel-like materials which produce oil in the lighter phase which tends to clog and restrict the flow of fluid in the tubing of blood analyzing equipment, especially in automatic blood analyzers. This patent also discloses a relatively more complicated arrangement which includes a spool member, such as of rubber, having a hole through it and which has a wiper for sealing contact with the inner wall of the tube. The spool moves toward the closed end of the tube while the gel-like material moves toward the stopper and closes the hole in the spool member upon separation of the phases.

In U.S. Pat. No. 3,909,419, a plasma separator is used wherein a pair of cylinders are disposed in the container and a plurality of micro encapsulated beads of gelatin are disposed between the cylinders. The specific gravities of the two cylinders and the gelatin beads are such that, by increasing the speed of the centrifuge after the phases have been separated, the cylinders move toward each other and rupture the encapsulated beads to cause the gelatin to form a seal between the cylinders and inner wall of the container at a location between the two phases. This arrangement is relatively expensive since it requires the manufacture of encapsulated beads and also requires centrifugation at two different speeds.

SUMMARY OF THE INVENTION

Accordingly, an object of the present invention is to provide a novel partitioning means for maintaining the lighter and heavier phases of a fluid, such as blood, separated, and which is highly effective, relatively simple, and economical. In accordance with the present invention, a fluid collection device is provided which includes a collection container for receiving a liquid adapted to be centrifugally separated into relatively lighter and heavier phases, a pair of movable members in the container each having a different specific gravity, and a sealant material disposed in contact with and between the members. The specific gravity of the two members together is intermediate the specific gravity of the lighter phase and that of the relatively heavy phase, and the specific gravity or the sealant is substantially equal to that of the two members together. The sealant is adapted to be squeezed outwardly from between the members and into contact with the interior wall of the container at a location between the separated phases. These as well as other objects and advantages of the present invention will become apparent from the following detailed description and drawing.

DESCRIPTION OF THE PREFERRED EMBODIMENT

Figure 1:
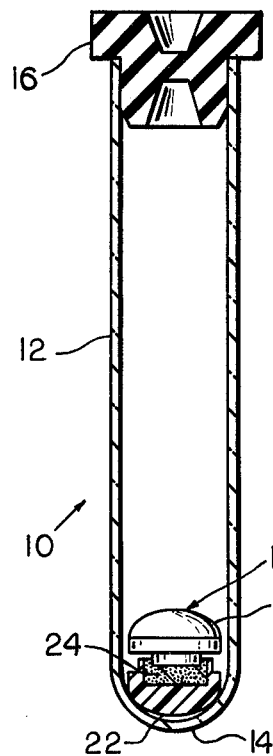
FIG. 1 is an elevational cross-sectional view of a blood collection tube containing a phase partitioning device in accordance with a preferred embodiment of the present invention.

Referring now to the drawing, and especially to FIGS. 1–4, there is shown a fluid collection device 10 including a container or blood collection tube 12 which is preferably of transparent glass and which is shown closed at the bottom by an integral portion 14 of the tube. The tube 12 has an upper open end that is closed by a closure or stopper 16 which extends into the open end in sealing engagement with the side walls of the tube. The stopper 16 is pierceable by a needle and self-sealing, and may be formed of a suitable elastomer, such as butyl rubber. The collection tube is provided with a desired negative pressure or partial vacuum that is maintained by the stopper 16. Disposed within the tube 12 is a movable blood phase partitioning or separation device 18 and which is shown alone in FIG. 2.

Figure 3:
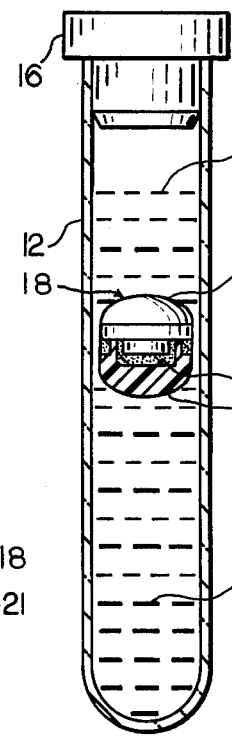
FIG. 3 is an elevational cross-sectional view of the collection tube of FIG. 1 after blood had been drawn into it and during an intermediate stage in the centrifugation of the blood.
Figure 4:
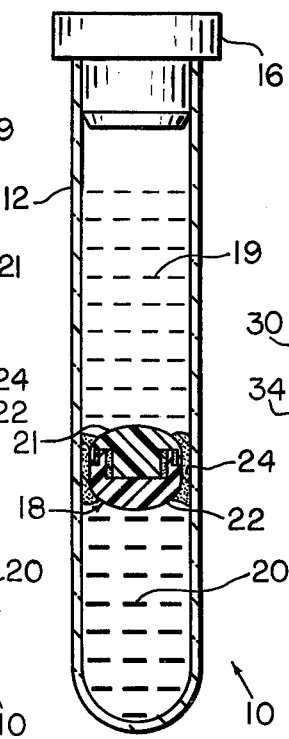
FIG. 4 is an elevational cross-sectional view of the collection tube shown in FIG. 3 after complete phase separation of the blood.

A sample of blood may be drawn into the blood collection device 10 by use of a double-ended needle cannula or a conventional needle holder and tube guide device (not shown) having a double-ended needle cannula. For example, after the distal pointed end of the needle cannula is inserted into the vein of a patient, the device 10 is moved within the holder until the proximal pointed end of the needle cannula has pierced the stopper 16 and communicates with the interior of the tube 12, whereupon blood flows into the tube. The filled tube is removed from the holder and placed in a centrifuge with the lower end 14 radially outwardly of the stopper and axis of rotation of the centrifuge. The phase separation device 18 will automatically move within tube 12 during centrifugation, for example, as illustrated in FIGS. 3 and 4, with the device 18 forming a partition or barrier across the tube (FIG. 4) upon complete separation of the blood into the lighter phase 19, serum or plasma, and the heavier cellular phase 20, as will be more fully discussed hereinafter.

The phase partitioning device 18 includes, as viewed in the drawing, upper and lower movable members 21 and 22, and a gel-like sealant material 24 disposed between the members 21 and 22 and which is adapted to be squeezed outwardly from between the members. The two members are formed so that the average specific gravity of the two members together is between the specific gravity of the separated lighter phase of blood, and that of the separated heavier cellular phase. Also, the sealant 24 is formed of a material, as will be further discussed, that has a specific gravity substantially equal to the average specific gravity of the two members 21 and 22 together. Because the specific gravity of the device 18, that is, of the two members 21 and 22, and sealant 24 together, is intermediate that of separated light and heavy phases, the device 18 will move during centrifugation and arrive at the interface of the two phases upon complete separation of the phases. The upper member 21 is made to have a specific gravity greater than that of the lower member 22 and is located radially inwardly toward the axis of rotation during centrifugation. Thus, during separation of the phases, as the density of the fluid below the device increases, and particularly as the device 18 approaches its final position, the two members 21 and 22 move toward each other extruding or squeezing the sealant 24 generally radially outwardly from below the lower extremities of the upper member 21 and into engagement with the interior walls of the tube at the interface of the two phases 19 and 20 so that the device 18 provides an annular, permanent partition or barrier sealing the separated phases from each other as seen in FIG. 4.

Figure 2:
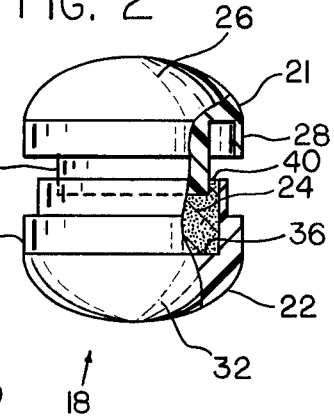
FIG. 2 is an enlarged elevational view, partly broken, of the phase partitioning device in FIG. 1.
Figure 5:
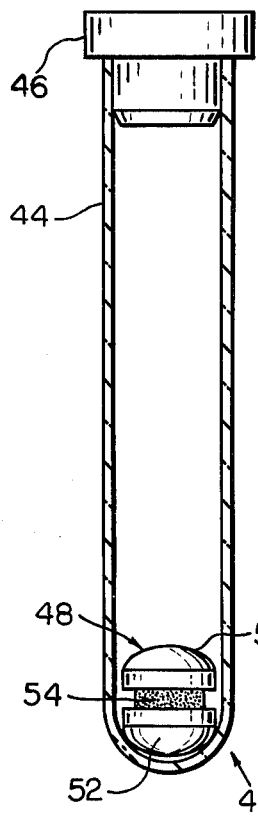
FIG. 5 is an elevational cross-sectional view of a blood collection tube having a phase partitioning device in accordance with a modified embodiment of the invention.

As indicated in FIG. 2, the upper member 21 of the partitioning device 18 has an upper portion 26 having a generally tapered or semi-spherical, domed upper surface with its highest point at the vertical axis of the device. The upper portion 26 is integral with an annular, peripheral portion 28 and an annular central piston portion 30 at the bottom of the member 21. The annular portion 28 and piston portion 30 are concentrically spaced from each other. The upper domed portion 26 of member 21 allows the blood cells to slide off and past the member to avoid the trapping of cells above the device. The bottom member 22 is generally cup-shaped and has a bottom tapered or domed portion 32 integrally connected with an annular, stepped, peripheral wall 34. The sealant material 24 is disposed within a cup-shaped, upper recess 36 in member 22 with the bottom side of the piston 30 normally facing and engaging the upper surface of the material 24. The bottom surface of the piston portion 30 and facing bottom surface of recess 36 are solid, flat, circular surfaces. The diameter of the piston portion 30 is substantially less than the diameter of the annular recess 36 so that when the members 21 and 22 move toward each other during centrifugation, the sealant 24 flows in the space between the side walls of recess 36 and the outer surface of piston 30. The upper portion of the wall 34 enters the annular space between the portions 28 and 30 but is spaced to permit flow of sealant from the device. More specifically, the sealant 24 moves generally radially outwardly across the bottom surfaces of the upper member 21 including the bottom surfaces of the piston portion 30 and bottom surfaces of annular portion 28 of member 21, as well as flowing across the upper end surface of the portion 34 of member 22, as viewed in the drawing. The sealant flows into contact with the interior wall of the tube with the sealant completely surrounding the members.

The sealant 24 is hydrophobic and inert with respect to the blood components, and is tacky or somewhat adherent to glass and plastics, and should hve a consistency or viscosity such that it is substantially non-flowable at rest or under normal handling conditions such as during tipping, mailing or shipping. Preferably, the sealant 24 includes principally a liquid hydrocarbon polymer, such as polybutene, liquid butyl, or liquid polybutadiene. A preferred sealant is a mixture of liquid polybutene and a filler of powder such as inert silica powder. A highly satisfactory mixture for use as a partitioning material 24 includes 100 parts by weight of liquid polybutene, known as Polybutene Grade 24, manufactured by the Chevron Chemical Company of San Francisco, Calif., 20 parts by weight of conventional hydrophillic silica powder ($SiO_2$) filler material, known as Min-U-Sil 10, manufactured by PGS (a subsidiary of ITT) of Pittsburg, Pennsylvania, and 9 parts by weight of a second silica powder known as Aerosil R-972, from Degussa Inc., Pigments Division, of New York, N.Y. The above Polybutene Grade 24 has a specific gravity of 0.898 at 60/60° F (ASTM D-287), and a viscosity of 40,000 SSU at 100° F (ASTM D-445 and D-446). The Min-U-Sil 10 powder has a specific gravity of about 2.65 and with the majority of it having a particle size below 10 microns. The Aerosil R-972 silica powder is a hydrophobic silica powder having a specific gravity of about 2.2 and an average size of about $20 \times 10^{-7}$ cm. This latter powder may be made hydrophobic by a process including flame hydrolysis of silica, and then reacting the silica with dimethyl dichlorosilane and steam in a fluidized bed reactor heated to about 400° C by means of an inert gas such as nitrogen (publication Chemiker-Zeitung/Chemische Apparatur 89 (1965), 437–440, Heidelberg/Germany). The specific gravity of the combined materials or mixture forming the separation material 18 was about 1.045 and had a viscosity or consistency such that it would not flow when the tube was tipped or mailed, but would flow during centrifugal separation of the phases when there was a suitable difference in specific gravity between the two associated members of the device. The viscosity of the sealant mixture may be varied by varing the proportions of the liquid hydrocarbon polymer and filler.

Since the specific gravity of whole blood is generally about 1.05, that of the light phase about 1.03, and that of the heavier phase about 1.08, the average or total specific gravity of the two members 21 and 22 together may be about 1.05. The specific gravity of the sealant material 24 can also be about 1.05, that is, approximately equal to the average specific gravity of the two members and which is intermediate the specific gravities of the light and heavy phases. The materials used in forming the members 21 and 22 should be inert with respect to the separated blood phases. Various types of materials are useful in forming the members 21 and 22, and each may be formed, for example, of one or more plastic materials, such as polycarbonate, polypropylene, a copolymer of methylmethacrylate and styrene, or the like. One member may be formed or molded of a different plastic material than the other associated so that the specific gravity of the upper member 21 is greater than that of the bottom member. For example, the upper member 21 may be molded for a copolymer of methylmethacrylate and styrene and have a specific gravity of about 1.13, while the lower member 22 is formed of polypropylene and have a specific gravity of about 0.9. By suitable proportioning the volumes of the two members, the average specific gravity is readily made to be between those of the separated light and heavy phases of blood.

When serum separation is required and the tube has only one end which is operable, such as tube 12, the outer diameter of the partitioning device 18 should be small enough relative to the inner diameter of the tube 12 to permit the passage of the blood clot past the device 18 where the device 18 is inserted prior to the introduction of blood. When plasma separation is required, an anti-coagulent, such as heparin, can be inserted in tube 12, such as during manufacture of the device 10, which will, of course, prevent a clot from forming so that the outer diameter of the partitioning device 18 may be close to the inner diameter of the glass tube 12. Where serum is to be separated and the outer diameter of the device 18 is close to the inner diameter of the collection tube such that the blood clot cannot pass by the device 18 during centrifugation, the device 18 may be inserted into the tube after the blood has been introduced or a double-ended tube may be used. For example, in tubes having two removable stoppers, one on each end, the whole blood can be inserted through one stopper of the tube containing device 18 and the device placed in a centrifuge such that the heavy phase moves toward that stopper. In this way, the serum (or plasma) can be removed after centrifugation by removal of the other stopper. In the latter case, as well as in the illustrated embodiment, the partitioning device 18 is, of course, inserted into the collection tube such that the movable member having the greater specific gravity, member 21, is radially inwardly of the other member 22 during centrifugation and will be adjacent the separated ligher phase in order that the two members move together and force the sealant 24 to flow radially outwardly.

As best seen in FIG. 2, the sealant 24 is normally substantially entirely enclosed by the piston portion 30 and the inner walls of recess 36. Only a relatively small surface area of the sealant, such as indicated at 40, is exposed to external fluids when the device 18 in its initial condition shown in FIGS. 1 and 2. Even during and after centrifugation, the surface area in contact with the separated phases 19 and 20 is relatively small since the members 21 and 22 provide a major portion of the device 18 in its final partitioning condition (FIG. 4). Thus, there is less chance of interaction between the sealant of 24 and the separated phases.

In the modified form of the invention illustrated in FIGS. 5-8, a blood collection device 43 is shown including a glass tube 44 having an upper open end closed by a rubber stopper 46, the tube and stopper being similar to the tube and stopper of collection device 10. Disposed in the tube 44 is a phase partitioning device 48 of modified construction.

Figure 6:
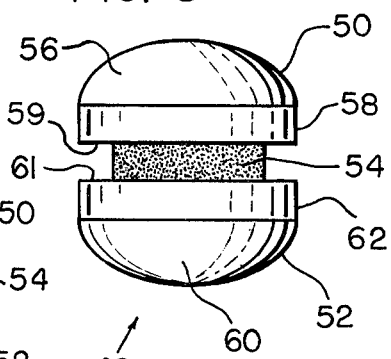
FIG. 6 is an enlarged elevational view of the phase partitioning device of FIG. 5.

As seen also in FIG. 6, partitioning device 48 includes upper and lower piston members 50 and 52 and a quantity of a hydrophobic gel-like sealant material 54 disposed between the members 50 and 52. The upper member has an upper domed portion 56 integral with a circular portion 58 which has a flat, solid bottom surface 59 in contact with sealant 54. The lower member has a bottom, domed portion 60 integrally connected with a circular portion 62 which has a flat, solid, circular upper surface 61 in contact with sealant 54 and which faces the flat circular bottom surface of member 50. The sealant material may be the same material as that of sealant material 24 discussed above in connection with the embodiment illustrated in FIGS. 1-4. The members 50 and 52 may also be formed of suitable plastics such as those previously mentioned herein. The specific gravity of the upper member 50 is greater than that of the lower member 52, while the specific gravity of the sealant 54 and the average specific gravity of the two members 50 and 52 are intermediate those of the separated lighter and heavier phases. For example the upper member 50 may be formed of polycarbonate and have a specific gravity of 1.2 while the lower member 52 may be formed of polypropylene and have a specific gravity of 0.9. Where the volumes of the two members 50 and 52 are equal, the average specific gravity of the two is, of course, 1.05 which may also be the specific gravity of the sealant 54.

Figure 7:
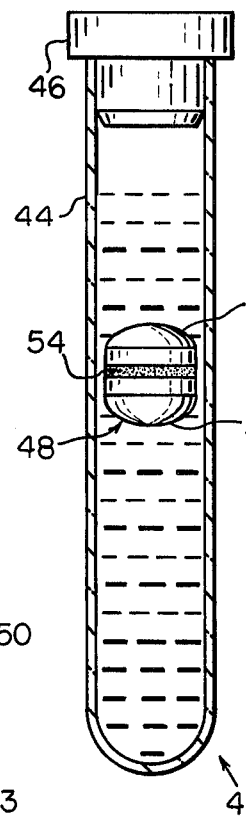
FIG. 7 is an elevational cross-sectional view of the collection tube of FIG. 5 during an intermediate stage in the centrifugation of blood in the tube.
Figure 8:
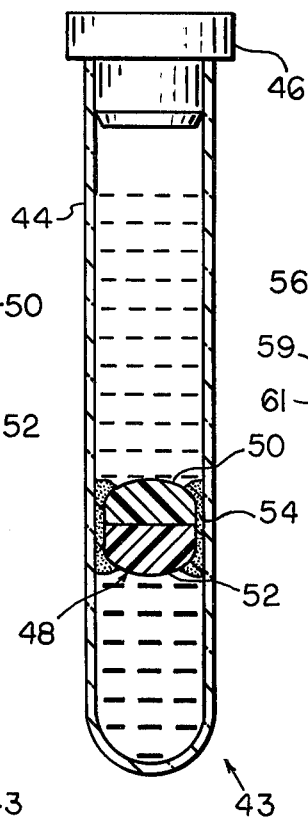
FIG. 8 is an elevational cross-sectional view of the collection tube shown in FIG. 7 after complete phase separation of the blood.

As illustrated in FIGS. 7 and 8, when blood has been introduced into the tube 44 and the tube centrifuged, the partitioning device 48 migrates to the interface of the phases or to a position between the phases. Because the member 50 has a greater specific gravity than that of member 52 and is radially inwardly with respect to the axis of rotation during centrifugation, the members move together as the phases become separated. The sealant 54 is extruded or squeezed outwardly into contact with the inner walls of the tube 44 with the two members and sealant forming a permanent partition across the tube to seal the phases from each other, as seen in FIG. 8.

In both partitioning devices 18 and 48, the sealant, as it is being squeezed out from the two associated members, flows generally radially outwardly past the facing sides or ends of the two members since this is the only flow path for the sealant in the illustrated embodiments. The sealant is displaced by the members and flows over the facing sides until the members engage each other.

The somewhat tacky sealant is in direct contact with bottom and top portions or facing sides of the two associated members of the partitioning devices 18 and 48 in their normal or initial conditions (FIGS. 1, 2, 5 and 6). In this way, the two members of each partitioning device are adhesively held together by the sealant so that the devices can be readily handled and inserted into collection tubes without separation of the members and without special means for holding the members and sealant together.

With the partitioning device 48, a somewhat greater surface area of sealant is in contact with external fluids in the initial condition of the device and before centrifugation than with device 18. However, the members 50 and 52 are of simpler configuration than members 21 and 22.

It was found that when the sealant was a mixture of liquid polybutene and a filter, such as given above by way of example, substantially no oil was introduced into the lighter phase that would clog or restrict flow of fluid in tubing associated with blood analyzers.

In partitioning device 18, the two members tend to be guided, for axial movement toward each other since the piston portion 30 enters the recess 36 so that a generally even distribution of sealant around the members is obtained. Other guides for device 18 and 48 can be used where desired to ensure that the sealant is evenly squeezed out from the members. For example, a central guide hole may be provided in one member for guidingly receiving a center guide pin on the associated member to maintain the facing surfaces of the members parallel as the sealant is squeezed radially outwardly toward the tube walls.

In each of the devices 18 and 48, an end surface at the bottom end of the upper member (21, 50) is axially spaced from and in facing relation with an end surface at the upper end of the lower member (22, 52) with the sealant in direct contact with these adjacent facing end surfaces. The sealant flows generally radially outwardly during centrifugation through spaces defined by adjacent or facing end surfaces of the members. The associated upper and lower members of each of the partitioning devices shown are completely axially spaced from each other with the sealant holding them together. The partitioning devices may be readily assembled by applying the sealant to one member and lightly touching the second member to the free surface of the sealant.

As various changes could be made in the above construction without departing from the scope of the invention, it is intended that all matter contained in the above description or shown in the accompanying drawing shall be interpreted as illustrative and not in a limiting sense.

What is claimed is:

1. A fluid collection device for receiving a liquid centrifugally separable into a lighter phase and a heavier phase during centrifugation of the device comprising a closed container, and phase partitioning means within said container including first and second axially spaced relatively movable members having a combined specific gravity intermediate that of the lighter phase and that of the heavy phase and with said first member having a specific gravity greater than that of said second member, one of said members including a cup-shaped portion having an inner bottom surface and inner side walls extending from said bottom surface to the open end of said cup-shaped portion, the other of said members having a piston portion with a surface normally in spaced facing relation with said bottom surface, and sealant material disposed in said cup-shaped portion between said bottom surface and said piston portion surface and in direct contact with both of said cup-shaped and piston portions, said sealant material having a specific gravity intermediate that of the lighter phase and that of the heavier phase, said piston portion being relatively movable in said cup-shaped portion toward said bottom surface to displace sealant material therefrom in response to the relative movement of said members toward each other due to centrifugal forces during centrifugation of the device, said cup-shaped and piston portions being sized and shaped such that sealant material flows axially within said cup-shaped portion in a direction toward the open end of said cup-shaped portion and radially outwardly into contact with the inner wall of said container to provide with said first and second members a partition sealing the heavier phase from the lighter phase.

2. The device of claim 1 wherein said sealant material is in direct contact with at least one of said members before centrifugation of the device.

3. A blood collection device for receiving a sample of blood adapted to be centrifugally separated into a lighter phase and a heavier cellular phase during centrifugation of the device comprising a container tube for receiving the sample of blood, said container being closed at each of the opposite ends thereof, and a phase partitioning device within said tube including first and second relatively movable members having a combined average specific gravity intermediate that of the lighter phase and that of the heavier cellular phase and with said first member having a specific gravity greater than that of said secone member, one of said members including a cup-shaped portion having an inner bottom surface and radially inner side walls extending from said bottom surface to the open end of said cup-shaped portion, the other of said members having a piston portion with a surface normally in spaced facing relation with said bottom surface, and sealant material disposed in said cup-shaped portion between said bottom surface thereof and said piston portion surface, said sealant material having a specific gravity substantially equal to said combined average specific gravity, said piston portion being relatively movable in said cup-shaped portion toward said bottom surface to displace sealant material therefrom in response to the relative movement of said members toward each other due to centrifugal forces during centrifugation of the device, said cup-shaped and piston portions being sized and shaped such that sealant material flows axially within said cup-shaped portion in a direction toward the open end of said cup-shaped portion and radially outwardly into contact with the inner wall of said tube to provide with said first and second members a partition sealing the heavier phase from the lighter phase.

4. The device of claim 3 wherein said sealant material is in direct contact with at least one of said members before centrifugation of the device.

5. The device of claim 4 wherein said sealant material is axially flowable between the radially outer side wall of said piston portion and the radially inner side wall of said cup-shaped portion during centrifugation of the device.

6. The device of claim 3 further including a needle pierceable stopper closing one of said opposite ends of said container tube for introducing blood into said container tube, and wherein said container tube has a negative pressure therein which is maintained by said stopper.

* * * * *